(12) United States Patent
Zorec (10) Patent No.: US 11,231,410 B2
(45) Date of Patent: Jan. 25, 2022

(54) METHOD FOR IDENTIFYING A COMPOUND USEFUL IN MITIGATING AND/OR THE TREATMENT OF A DISEASE ASSOCIATED WITH ABNORMAL ASTROCYTIC FUNCTION

(71) Applicant: Celica BIOMEDICAL, Ljubljana (SI)

(72) Inventor: Tomaž Mark Zorec, Ljubljana (SI)

(73) Assignee: Celica BIOMEDICAL, Ljubljana (SI)

( * ) Notice: Subject to any disclaimer, the term of this patent is extended or adjusted under 35 U.S.C. 154(b) by 407 days.

(21) Appl. No.: 15/766,020

(22) PCT Filed: Oct. 6, 2016

(86) PCT No.: PCT/EP2016/073904
§ 371 (c)(1),
(2) Date: Apr. 5, 2018

(87) PCT Pub. No.: WO2017/060367
PCT Pub. Date: Apr. 13, 2017

(65) Prior Publication Data
US 2018/0284101 A1    Oct. 4, 2018

(30) Foreign Application Priority Data
Oct. 6, 2015    (EP) .................................... 15188662

(51) Int. Cl.
| | | |
|---|---|---|
| G01N 33/53 | (2006.01) | |
| G01N 33/50 | (2006.01) | |
| G01N 33/68 | (2006.01) | |
| G16C 10/00 | (2019.01) | |

(52) U.S. Cl.
CPC ..... *G01N 33/5058* (2013.01); *G01N 33/6896* (2013.01); *G16C 10/00* (2019.02); *G01N 2333/726* (2013.01)

(58) Field of Classification Search
None
See application file for complete search history.

(56) References Cited

U.S. PATENT DOCUMENTS

2018/0231525 A1 *    8/2018    Vardjan ................ A61K 31/138

FOREIGN PATENT DOCUMENTS

EP    2 818 177 A1    12/2014

OTHER PUBLICATIONS

International Search Report for corresponding International Application No. PCT/EP2016/073904 dated Feb. 10, 2017.
Written Opinion of the International Searching Authority for corresponding International Application No. PCT/EP2016/073904 dated Feb. 10, 2017.
Ahmed et al., "GPR109A, GPR109B and GPR81, a family of hydroxy-carboxylic acid receptors", Trends in Pharmacological Services, vol. 30, No. 11, 2009, pp. 557-562.
Ahmed et al., "An Autocrine Lactate Loop Mediates Insulin-Dependent Inhibition of Lipolysis through GPR81", Cell Metabolism Article, ELL METAB, (2010), vol. 11, Apr. 7, 2010, pp. 311-319.
Vardjan et al., "Dynamcs of beta-Adrenergic/cAMP Signaling and Morphological Changes in Cultured Astrocytes", GLIA, vol. 62, 2014, pp. 566-579.
Berendsen et al., "GROMACS: A message-passing parallel molecular dynamics implementation", Computer Physics Communications, vol. 91, 1995, pp. 43-56.
Dvorak et al., "Identification of Hydroxybenzoic Acids as Selective Lactate Receptor (GPR81) Agonists with Antilipolytic Effects", ACS Medicinal Chemistry Letters, vol. 4, 2012, pp. 637-639.
Guex et al., "SWISS-MODEL and the Swiss-Pdb Viewer: An environment for comparative protein modelling", Electrophoresis, vol. 18, 1997, pp. 2714-2723.
Henke et al., "Glycogen Phosphorylase Inhibitors", Mini-Reviews in Medicinal Chemistry, vol. 6, 2006, pp. 845-857.
Hess et al., "GROMACS 4: Algorithms for Highly Efficient, Load-Balanced, and Scalable Molecular Simulation", Journal of Chemical Theory and Computation, vol. 4, 2008, pp. 435-447.
Kiefer et al., "The SWISS-MODEL Repository and associated resources", Nucleic Acids Research, vol. 37, 2009, pp. D387-D392.
Kopp et al., "The SWISS-MODEL Repository of annotated three-dimensional protein structure homology models", Nucleic Acids Research, vol. 32, 2004, pp. D230-D234.
Kreft et al., "Properties of Ca(2+)-Dependent Exocytosis in Cultured Astrocytes", GLIA, vol. 46, 2004, pp. 437-445.
Kuei et al., "Study of GPR81, the Lactate Receptor, from Distant Species Identifies Residues and Motifs Critical for GPR81 Functions", Molecular Pharmacology, vol. 80, 2011, pp. 848-858.
Lauritzen et al., "Lactate Receptor Sites Link Neurotransmission, Neurovascular Coupling, and Brain Energy Metabolism", Cerebral Cortex Advance Access, 2013, pp. 1-12.
Lindhal et al., "GROMACS 3.0: A package for molecular simulation and trajectory analysis", J Mol Model, Vo. 7, 2001, pp. 306-317.

(Continued)

*Primary Examiner* — Michael D Pak
(74) *Attorney, Agent, or Firm* — Renner, Otto, Boisselle & Sklar, LLP (57) ABSTRACT

The present invention pertains to a method for identifying a compound that can be used in mitigating and/or the treatment of a disease associated with abnormal astrocytic function, said method comprising: (i) providing a compound; (ii) determining whether said compound is a ligand for the GPR81 receptor by determining said compound's binding energy with the GPR81 receptor using molecular dynamics (MD) simulations and comparing said binding energy to the binding energy determined for a reference compound (such as L-lactate) with the GPR81 receptor; and (iii) if said compound is determined to be a ligand for the GPR81 receptor, bringing said compound in contact with a living astrocyte and determining the cAMP level in said astrocyte contacted with said compound. The present invention further pertains to an agent elevating the cAMP level in astrocytes for use in mitigating and/or in the treatment of a disease associated with abnormal astrocytic function.

4 Claims, 9 Drawing Sheets

(56) References Cited

OTHER PUBLICATIONS

Liu et al., "3,5-Dihydroxybenzoic Acid, a Specific Agonist for Hydroxycarboxylic Acid 1, Inhibits Lipolysis in Adipocytes", The Journal of Pharmacology and Experimental Therapeutics, 2012, vol. 341, No. 3, pp. 794-801.
Parpura et al., "Gliotransmission: Exocytotic release from astrocytes", Brain Res Rev., vol. 63, May 2010, pp. 33-92.
Peitsch, "Protein Modeling by E-mail", Bio/Technology, vol. 13, Jul. 1995, pp. 658-660.
Pettersen et al., "UCSF Chimera-A Visualization System for Exploratory Research and Analysis", Journal of Computational Chemistry, vol. 25, No. 13, 2004, pp. 1605-1612.
Schwede et al., "SWISS-MODEL: An automated protein homology-modeling server", Nucleic Acids Research, vol. 31, No. 13, 2003, pp. 3381-3385.
Schuttelkopf et al., "PRODRG: a tool for high-throughput crystallography of protein-ligand complexes", Acta Crystallographica Section D, Biological Crystallography, 2004, pp. 1355-1363.
Van Der Spoel et al.,"GROMACS: Fast, Flexible and Free", Journal of computational Chemistry, vol. 26, No. 16, 2005, pp. 1701-1718.
Mosienko et al., "Is L-lactate a novel signaling molecule in the brain?", Journal of Cerebral Blood Flow & Metabolish, vol. 35, 2015, pp. 1069-1075.
Vardjan et al., "Chapter 5—Regulated Exocytosis in Astrocytes is as Slow as the Metabolic Availability of Gliotransmitters: Focus on Glutamate and ATP", Springer, 2014, Glutamate and ATP at the Interface of Metabolism and signaling in the Brain, Advances in Neurobiology 11, pp. 81-101.
Vardjan et al., "Pathologic Potential of Astrocytic Vesicle Traffic: New Targets to Treat Neurologic Diseases?", Cell Transplantation, vol. 24, 2015, pp. 599-612.
Vardjan et al., "Excitable Astrocytes: Ca(2+)- and cAMP-Regulated Exocytosis", Neurochem Res., 2015, pp. 1-11.
Verkhratsky et al., "Astrogliopathology in neurological, neurodevelopmental and psychiatric disorders", Neurobiol Dis., vol. 85, Jan. 2016, pp. 254-261.
Schwartz et al., "Preparation and Characterization of Type 1 Astrocytes Cultured From Adult Rat Cortex, Cerebellum, and Straitum", GLIA, vol. 5, 1992, pp. 75-80.
Tautermann et al., "What can we learn from molecular dynamics simulations for GPCR drug design?", Computational and Structural Biotechnology Journal, vol. 13, 2015, pp. 111-121.
Bermudez et al., "Structure versus function—The impact of computational methods on the discovery of specific GPCR-ligands", Bioorganic & Medicinal Chemistry, vol. 23, 2015, pp. 3907-1912.
Bekker et al., "Gromacs: A parallel Computer for Molecular Dynamics Simulations", Physics Computing '92: Proceedings of the 4th International Conference, Aug. 24-28, 1992, pp. 252-256.

* cited by examiner

METHOD FOR IDENTIFYING A COMPOUND USEFUL IN MITIGATING AND/OR THE TREATMENT OF A DISEASE ASSOCIATED WITH ABNORMAL ASTROCYTIC FUNCTION

This application is a national phase of International Application No. PCT/EP2016/073904 filed Oct. 6, 2016, and claims priority to European Application No. 15188662.9 filed on Oct. 6, 2015, which are incorporated herein by reference.

FIELD OF THE INVENTION

The present invention relates to pharmaceutically active substance targets and mechanisms for regulating the L-lactate specific G-protein coupled receptor (GPCR), GPR81 receptor (also known as HCAR1). This receptor is coupled to cAMP signaling, a key second messenger involved in a number of neuropathological conditions. The invention also relates to the reference method of selecting ligands based on determining binding interaction of molecules, putative ligands of the GPR81 receptor, and on measurements of cytosolic levels of cAMP in astroglial cells.

This invention includes specific molecular dynamics simulations (MD) and experiments where cytosolic levels of cAMP ($[cAMP]_i$) were measured by fluorescence nanosensors in cultured astrocytes. Moreover, cAMP also affects glucose and glycogen metabolism in astrocytes, hence cAMP represents a link between GPCRs and glycogen metabolism, which generates energy fuel in the process of glycolysis and generates precursor signaling molecules, such as glutamate. L-lactate (lactate), an end product of glycolysis is primarily synthesized in the central nervous system (CNS) by astrocytes, a type of glial cells, abundantly present in the brain. Recently, it has been shown that lactate may not only play a role as an energy metabolite but may also act as a signaling molecule through cell surface receptors to modulate the function of CNS. The receptor via which lactate may affect the function of CNS, GPR81 (alias HCAR 1), was originally discovered in adipocytes and was shown to couple to cAMP signaling. The same receptor was also found to be present in neurons and astrocytes. Here we investigated the binding characteristics of different ligands for this receptor. Using Molecular Dynamics simulation (MD) we estimated the stability of various ligand-receptor complexes and ranked the selected ligand molecules according to their apparent binding affinity. While the used MD approach revealed consistency with the experimental data published (Dvorak et al. 2012), our results unexpectedly revealed that some of the molecules that showed no efficacy in the study of Dvorak et al (2012), also exhibited strong binding interactions. Therefore, we compared the MD data with measurements of cytosolic cAMP in single astrocytes, as a readout of efficacy, where several of assumed molecules not to be effective for GPR81 binding, were applied to astrocytes. Importantly, these results revealed that molecules that were shown previously not to be effective in an in vitro receptor activity assay (Dvorak et al. 2012), strongly activated cellular cAMP signaling. The new approach of MD and the monitoring downstream receptor cAMP signaling is thus a suitable new method for selecting GPR81 binding ligands as potential pharmacologic modulators of astrocytic metabolic response, which may be altered in neuropathological states including neurodevelopmental, neurodegenerative and neurotraumatic states.

BACKGROUND OF THE INVENTION

Astrocytes

Neurons in the peripheral and central nervous system (CNS) are surrounded by glial cells, discovered in the mid-19th century. Among the glial cells in the vertebrate CNS astrocytes are abundant and heterogeneous and they have been first described in more detail in the 20th century. Traditional view, generated 100 years ago, holds that glial cells merely provide structural support to neurons. However, during the last two decades experimental evidences have shown that astrocytes are considered active partners in cell-to-cell signaling. Astrocytes can be broadly defined as primary homeostatic cells of the brain responsible for a wide variety of functions that include for example the regulation of synaptogenesis, synaptic maturation, neurotransmitter homeostasis, brain microcirculation, brain metabolism and control over formation and maintenance of the blood-brain barrier. Therefore, they contribute to most if not all of neuropathological conditions (Vardjan et al. 2015; Verkhratsky and Parpura 2015).

These new communication functions of astrocytes depend partly on the mechanisms by which astrocytes interact with the surrounding cells. These include plasma membrane channels, receptors, transporters, and mechanisms that include exo- and endocytotic vesicles. The latter processes participate in maintaining the quality of the plasma membrane signaling capacity and in the release of signaling molecules—chemical transmitters, glio-signaling molecules—which may affect the function of neighboring cells in health and disease processes (Parpura and Zorec 2010; Vardjan and Zorec 2015).

It is now clear that the properties of $Ca^{2+}$-dependent fusion of the vesicle membrane with the plasma membrane in astrocytes and in neurons, monitored by membrane capacitance techniques, differ mainly in the kinetics. In astrocytes regulated exocytosis is orders of magnitude slower than in neurons (Kreft et al. 2004; Vardjan et al. 2015). The relatively slow kinetics of regulated exocytosis in astrocytes likely involves vesicle dynamics regulation and mechanisms governing the merger of the vesicle membrane with the plasma membrane, but may also depend on the availability of gliotransmitters such as ATP and glutamate in metabolic pathways for packaging into vesicles via specific vesicle transporters (Vardjan et al. 2014b).

The concentration of ATP and glutamate in the cytoplasm is in the range of millimoles per liter, sufficiently high to support loading into vesicles via specific vesicle transporters, VNUT and VGLUTs, respectively. Both ATP and glutamate are associated with the metabolism of glucose, which is linked to glycogen. The glycogen reservoir via glycogen shunt in astrocytes can provide fuel for energy production during hypoglycemia, as well as during normal brain metabolism. Incubation of astrocytes with diaminobenzidine (DAB), a glycogen phosphorylase A inhibitor (Henke and Sparks 2006), inhibits the glycogen shunt. Glycolysis and glycogenolysis seem to provide most of the energy required during an abrupt energy demand. The glycogen serves as the source of lactate, which may be transferred to neurons or converted to pyruvate, which enters the Krebs cycle.

It has been shown recently that lactate may not only play a role as a metabolite but may act via a surface receptors to modulate the function of CNS (Lauritzen et al. 2013). The receptor via which lactate may affect the function of CNS, GPR81, was originally discovered in adipocytes (Ahmed et al. 2009; Ahmed et al. 2010). Although it is assumed that in the CNS GPR81 receptor mediates a reduction in the concentration of cAMP (Lauritzen et al. 2013), this has never been directly demonstrated. However, recent results from our laboratories have shown that the dynamics of cAMP in astrocytes upon GPR81 receptor activation is directly affected (European Patent Application No. 13 173 446.9; Mechanism and Drug Targets for Reducing Cell Edema (Neuroprotection) and Cytoplasmic Excitability in Astrocytes in Normal and Pathological States), studied by using an advanced real-time optophysiological approach with FRET nano-sensors (Vardjan et al. 2014a). Here we describe the method for screening of GPR81 receptor binding ligands. The estimated binding energy is ranked and experimental studies have been carried out to see whether the effectiveness of these ligands is correlated to the estimated ligand receptor interaction.

GPR81-Binding Ligands

Previously Kuei et al. (Kuei et al. 2011) described a structural homology model for human GPR81 and performed molecular dynamics simulation and mutation studies to define the active site of the membrane-nested protein. According to their study Arg71, Arg99, Arg240 and Glu166 are the key amino acid residues for ligand protein interaction that results in receptor activation (Kuei et al. 2011).

The GPR81 receptor can be activated with hydroxybenzoic acid derivates, as determined with the GTPγS binding assay and the inhibition of cAMP accumulation assay (in HCA1 expressing and non-expressing cells) (Liu et al. 2012). Their experimental results show that 3,5-dihydroxybenzoic (3,5-DHBA) acid is a selective agonist for human HCA1 (compared versus HCA2, with 3,5-DHBA, 3,4-DHBA, 2,3-DHBA, 3,4,5-DHBA). An additional docking study exposed a structural difference in the binding site for the HCA1 compared to HCA2 and HCA3 and furthered the understanding on the type of interactions necessary for the activation (Liu et al. 2012). Then the activation of human HCAR1 was studied with different ligands, mostly derivates or similars to hydroxybenzoic acid and $EC_{50}$ values for different ligands were reported (Dvorak et al. 2012).

SUMMARY OF THE INVENTION

Figure 1:
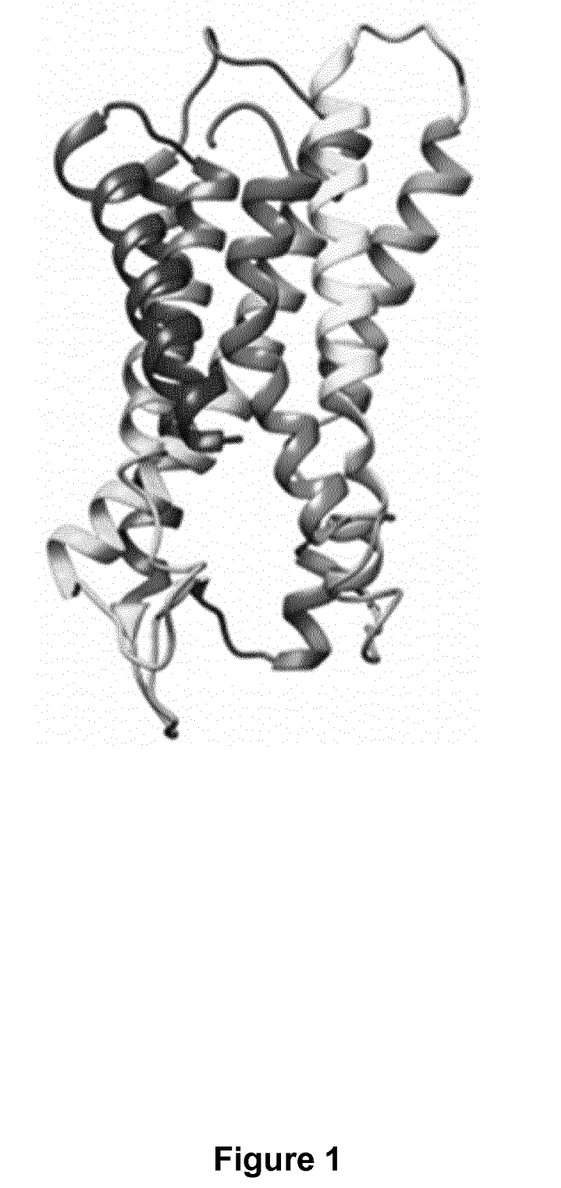
FIG. 1: Model receptor structure (GPR81, Q9BXC0: 9606.ENSP0000034).

The invention is based on the previously unrecognized relationship between the binding energy of ligands of GPR81 receptor and cAMP level in living cells, a second messenger relating to a number of specific neural disorders (European Patent Application No. 13 173 446.9; Mechanism and Drug Targets for Reducing Cell Edema (Neuroprotection) and Cytoplasmic Excitability in Astrocytes in Normal and Pathological States). For example, the inventor was the first to observe that some ligands for GPR81, that were shown previously to be inefficient, have a potent action on living astrocytes in which cAMP is monitored, a second messenger coupled to GPR81 receptor. This conclusion is based on the use of molecular dynamics modelling, similar to the one developed previously (Kuei et al. 2011). The model structure of GPR81 (HCAR1) was obtained from the SWISS-MODEL repository (Guex and Peitsch 1997; Kiefer et al. 2009; Kopp and Schwede 2004; Peitsch 1995; Schwede et al. 2003) (FIG. 1). This model was used since it included: the longest sequence of amino-acid residues, also found in the model of Kuei at al., and the amino-acid residues, that are relevant for receptor activation (Kuei et al. 2011).

The candidate substances tested in this study are listed in Table 1. Each ligand was energy minimized and manually docked into the assumed region of the receptor's active site. For this boundary conditions in the model were set as follows: the protein-ligand complex was immersed in water and sodium ions to compensate any negative charges. With the ligand constrained, the system was heated to 309 K (36° C.) and equilibrated at 1 bar. Ligand constraints were then removed and routines for molecular dynamics (MD) simulations were run. To estimate stability of receptor-ligand complexes potential energies were examined. MD simulations were performed with GROMACS 4.6.5 (Bekker et al. 1992; Berendsen et al. 1995; Hess et al. 2008; Lindhal et al. 2001; van der Spoel et al. 2005), molecular rendering was done with UCSF Chimera 1.9 (Pettersen et al. 2004). Topology files were prepared utilizing the GROMOS 43a1 united atom force field, where the topologies for ligands were obtained through PRODRG (Schüttelkopf and van Aalten 2004).

TABLE 1

List of tested ligands with chemical formulae, IUPAC names, their designations within this study.

| Ligand designation | Chemical name | Structural formula |
|---|---|---|
| "propfos" | (3,5-dihydroxyphenyl) propylphosphinic acid | |
| "3cl5hi" | 3-chloro-5-hydroxybenzoic acid | |
| "3f5hi" | 3-fluoro-5-hydroxybenzoic acid | |
| "but" | 3-tertbutyl-5-hydroxybenzoic acid | |
| "butfos" | (3,5-dihydroxyphenyl)(tertbutyl) phosphinic acid | |

TABLE 1-continued

List of tested ligands with chemical formulae, IUPAC names, their designations within this study.

| Ligand designation | Chemical name | Structural formula |
|---|---|---|
| "etfos" | (3,5-dihydroxyphenyl) ethylphosphinic acid | |
| "fos" | (3,5-dihydroxyphenyl) phosphinic acid | |
| "mefos" | (3,5-dihydroxyphenyl) methylphosphinic acid | |
| "metoxi" | 3-methoxy-5-hydroxybenzoic acid | |
| "lakta" | Lactic acid/lactate | |
| "oh" | 3,5-dihydroxybenzoic acid | |
| "ph" | 3-phenyl-5-hydroxybenzoic acid | |

Unexpectedly, the results of MD revealed significant binding energies indicative for ligand binding to GPR81, although previous studies (Dvorak et al., 2012) indicated ligands may not be effective in vivo at al. Therefore, we used an in vivo (in situ) assay based on measuring cytosolic second messenger cAMP in living cells. As described in the previous European Patent Application No. 13 173 446, the cAMP level may, be determined by fluorescence nanosensors in the astrocyte. In particular, the cAMP level may be determined by expressing the plasmid for FRET construct Epac1-camps or AKAR2. FRET signal is reported as the ratio of YFP to CFP fluorescence signal. The change in FRET signals reflects change in [cAMP]i. The inventions comprises of using MD and cAMP measurements.

The present invention may thus be summarized according to the following items 1 to 15:

1. A method for identifying a compound that can be used in mitigating and/or the treatment of a disease associated with abnormal astrocytic function, said method comprising:
   (i) providing a compound;
   (ii) determining whether said compound is a ligand for the GPR81 receptor by determining said compound's binding energy with the GPR81 receptor using molecular dynamics (MD) simulations and comparing said binding energy to the binding energy determined for a reference compound (such as L-lactate) with the GPR81 receptor; and
   (iii) if said compound is determined to be a ligand for the GPR81 receptor, bringing said compound in contact with a living astrocyte and determining the cAMP level in said astrocyte contacted with said compound.

2. The method according to item 1, wherein said compound is determined to be a ligand for the GPR81 receptor, if it shows a cutoff criterion (CC) of ≥1, estimated by using absolute values of binding energies, using the equation: CC=(binding energy of compound)/(binding energy of reference compound).

3. The method according to item 1 or 2, wherein said compound is identifying as being a compound that can be used in mitigating and/or the treatment of a disease associated with abnormal astrocytic function, if the steady state change in cAMP level is larger than the 3 standard deviations of the signal of cAMP level.

4. The method according to any one of items 1 to 3, wherein the disease associated with abnormal astrocytic function is selected from the group consisting of: Alzheimer's disease, encephalitis, brain tumours, glioma, brain trauma, concussion, epilepsy, autism, multiple sclerosis, meningoencephalitis, sleep disorders, stroke, Parkinson's disease, spinal cord injury, lipid storage disease.

5. An agent elevating the cAMP level in astrocytes for use in mitigating and/or in the treatment of a disease associated with abnormal astrocytic function, such as neurodevelopmental, neurodegenerative, neuroinflammatory and neurotraumatic conditions.

6. The agent for use according to item 5, wherein said agent is an agonist for a lactate receptor.

7. The agent for use according to item 6, wherein said agent is an agonist for the lactate receptor GPR81.

8. The agent for use according to any one of items 5 to 7, wherein said agent is selected from the group consisting of lactate, such as D-lactate or L-lactate, hydroxybenzoic acid, such as 3-hydroxy benzoic acid, 3-hydroxy-5-substituted benzoic acid, such as 3-Chloro-5-hydroxybenzoic acid (3-Cl-5-HBA), 3-hydroxy butyrate, 3-hydroxy-yoctanoate, 3H-imidazo[4,5-b] pyridin-5-ols, and 4-Methyl-N-(5-(2-(4-methylpiperazin-1-yl)-2-oxoethyl)-4-(2-thienyl)-1,3-thiazol-2-yl)cyclohexanecarboxamide, 4-Methyl-cyclohexanecarboxylic acid {5-[2-(4-methyl-piperazin-1-yl)-2-oxo-ethyl]-4-thiophen-2-yl-thiazol-2- yl}-amide, 4-Methyl-N-(5-(2-(4-methylpiperazin-1-yl)-2-oxoethyl)-4-(5-chloro-thiophen-2-yl)-1,3-thiazol-2-yl)cyclohexanecarboxamide, and 4-Methyl-cyclohexanecarboxylic acid {4-(5-chloro-thiophen-2-yl)-5-[2-(4-methyl-piperazin-1-yl)-2-oxo-ethyl]-thiazol-2-yl}-amide.

9. The agent for use according to any one of items 5 to 8, wherein said agent is lactate, such as D-lactate or L-lactate.
10. The agent for use according to any one of items 5 to 8, wherein said agent is hydroxybenzoic acid, such as 3-hydroxy benzoic acid or 3-hydroxy-5-substituted benzoic acid, such as 3-Chloro-5-hydroxybenzoic acid (3-Cl-5-HBA).
11. The agent for use according to any one of items 5 to 8, wherein said agent is 3-hydroxy butyrate.
12. The agent for use according to any one of items 5 to 8, wherein said agent is 3-hydroxy-yoctanoate.
13. The agent for use according to any one of items 5 to 8, wherein said agent is a 3H-imidazo[4,5-b] pyridin-5-ol.
14. The agent for use according to any one of items 5 to 8, wherein said agent is selected from the group consisting of: 4-Methyl-N-(5-(2-(4-methylpiperazin-1-yl)-2-oxoethyl)-4-(2-thienyl)-1,3-thiazol-2-yl)cyclohexanecarboxamide, 4-Methyl-cyclohexanecarboxylic acid {5-[2-(4-methyl-piperazin-1-yl)-2-oxo-ethyl]-4-thiophen-2-yl-thiazol-2-yl}-amide, 4-Methyl-N-(5-(2-(4-methylpiperazin-1-yl)-2-oxoethyl)-4-(5-chloro-thiophen-2-yl)-1,3-thiazol-2-yl)cyclohexanecarboxamide, and 4-Methyl-cyclohexanecarboxylic acid {4-(5-chloro-thiophen-2-yl)-5-[2-(4-methyl-piperazin-1-yl)-2-oxo-ethyl]-thiazol-2-yl}-amide.
15. The agent for use according to any one of items 5 to 14, wherein the disease associated with abnormal astrocytic function is selected from the group consisting of: Alzheimer's disease, encephalitis, brain tumours, glioma, brain trauma, concussion, epilepsy, autism, multiple sclerosis, meningoencephalitis, sleep disorders, stroke, Parkinson's disease, spinal cord injury, lipid storage disease.

BRIEF DESCRIPTION OF THE DRAWINGS

FIG. 9: shows that astrocytes express GPR81 receptor for lactate and that the treatment of astrocytes with GPR81 receptor agonists, endogenous lactate or exogenous 3-Chloro-5-hydroxybenzoic acid (3-Cl-5-HBA), a specific agonist for GPR81, increases intracellular cAMP levels in astrocytes. (a) Expression of GPR81 receptors in cultured rat astrocytes. Fluorescence image of astrocyte cell immunostained with antibodies against GPR81 receptor (GPR81) and transmitted light (TL) image of the same cell. Scale bar: 20 µm. (b-d) FRET measurements of cAMP in living primary astrocytes transfected with (b) Epac1-camps and (c-d) AKAR2 cAMP nano-sensors. Time-course of average YFP/CFP emission ratio after addition of (b-c) 20 mM lactate and (d) 500 µM 3-Cl-5-HBA at t=0. Data are expressed as the YFP/CFP fluorescence emission ratio normalized to the baseline ratio values (ratio YFP/CFP). Numbers in the brackets depict the number of independent experiments. Note that the increase in intracellular cAMP levels after stimulation in (b) is reflected by the monophasic decline in FRET signal (ratio YFP/CFP) and in (c,d) by monophasic uprise in FRET signal. Each data represents mean±s.e.m. From European Patent Application No. 13 173 446, FIG. 6.

DETAILED DESCRIPTION OF THE INVENTION

To evaluate the efficiency of binding of GPR81 ligands we here used a computational screening approach to establish potential differences in binding capacity of selected GPR81 ligands of HCAR1 (Table 1).

If a ligand binds to the receptor and the nature of the interaction induces a conformational change that results in an activation of the receptor greater or equal to the activation yielded by an endogenous signaling molecule (L-lactate), then it can be classified as an agonist—and vice versa—if a ligand binds and elicits a smaller activation response than L-lactate, it can be considered as an antagonist candidate in principle. As the work of Dvorak et al. (Dvorak et al. 2012) provides information on the degree of receptor activation, possible antagonist candidates were selected on the basis of EC50 values for the ligands presented therein. Some ligands were added to the test set based on their structural similarities. Molecular Dynamics (MD) simulation was performed and results compared qualitatively vs. a test set of 3-chloro-5-hydroxybenzoic acid and L-lactate.

Thus, in one aspect the invention relates to a method for identifying a compound that can be used in mitigating and/or the treatment of a disease associated with abnormal astrocytic function, said method comprising:
  (i) providing a compound;
  (ii) determining whether said compound is a ligand for the GPR81 receptor by determining said compound's binding energy with the GPR81 receptor using molecular dynamics (MD) simulations and comparing said binding energy to the binding energy determined for a reference compound (such as L-lactate) with the GPR81 receptor; and
  (iii) if said compound is determined to be a ligand for the GPR81 receptor, bringing said compound in contact with a living astrocyte and determining the cAMP level in said astrocyte contacted with said compound.

Preferably, a compound is determined to be a ligand for the GPR81 receptor, if its binding energy determined by molecular dynamics (as used in the present invention), equals or is better than that determined for the reference compound (such as L-lactate). More specifically, a compound is determined to be a ligand for the GPR81 receptor, if its binding energy determined by molecular dynamics is more negative than that determined for the reference compound (such as L-lactate).

According to certain embodiments, a compound is determined to be a ligand for the GPR81 receptor, if it shows a cutoff criterion (CC) of ≥1, estimated by using absolute values of binding energies, using the equation: CC=(binding energy of compound)/(binding energy of reference compound).

According to certain embodiments, the reference compound is L-lactate.

If a compound is considered to be an effective ligand for the GPR81 receptor, astrocytes, which carry the GPR81 receptor, are exposed to the candidate compound and the effect of the compound is monitored. At rest the level of cAMP is stable, but noisy. The level of noise is estimated by determining standard deviation of the noise. When the compound is applied the effectiveness of it is considered when the steady state change in cAMP level is larger than the 3 standard deviations of the signal of cAMP level.

According to certain embodiments, the compound is identifying as being a compound that can be used in mitigating and/or the treatment of a disease associated with abnormal astrocytic function, if the steady state change in cAMP level is larger than the 3 standard deviations of the signal of cAMP level.

In MD simulations relative convergence was attained within the last 300-1000 time-steps on the energy diagrams. The values in FIGS. 3, 4, 5 and 6 are therefore based on the potential energies in the last 200 time-steps. All diagrams show energy values for each one of the tested ligands in terms of box-plots, where the designations of the ligands are explained in Table 1.

MD simulation packages, such as GROMACS normally use the concept of different potentials to characterize pairwise interactions between particles. In essence, potentials are used for three types of interaction: i.) bonded interaction, ii.) non-bonded interaction and iii.) restraints; the first two groups are self-explanatory due to their names, the third one handles different movement, position or angle restraints that can be imposed to a part of the simulated system. Under the assumption that ligand-receptor binding occurs in a non-covalent manner, these then represent non-bonded interaction potentials.

Figure 2:
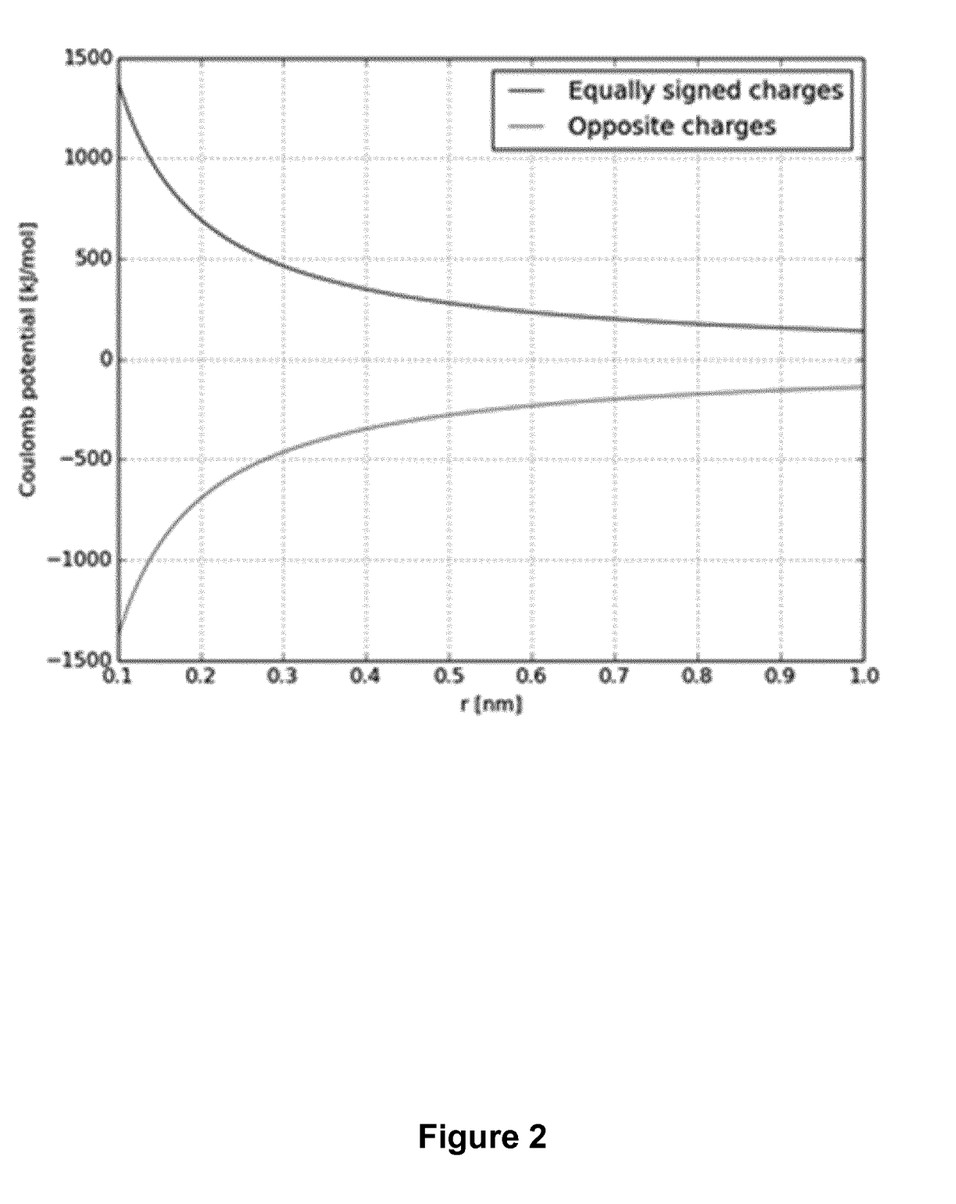
FIG. 2: Coulomb potential for interaction between two atoms as a function of separation distance.
Figure 3:
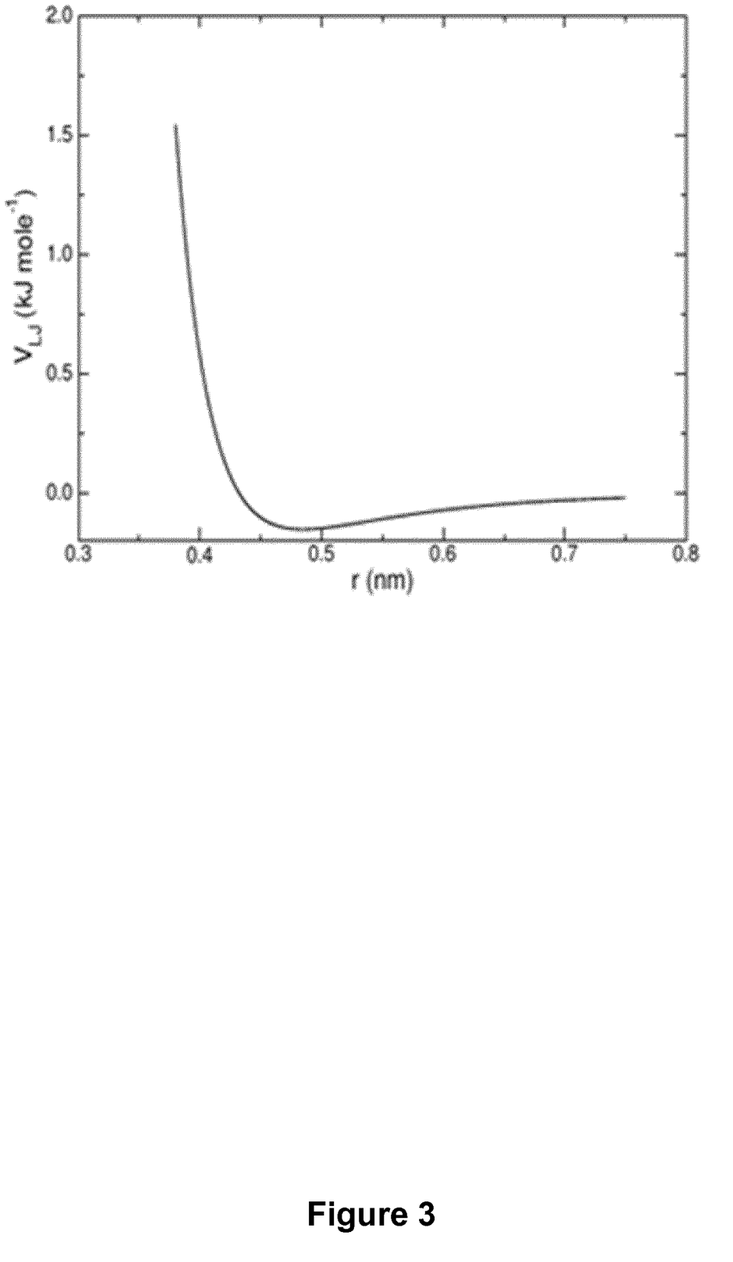
FIG. 3: Lennard-Jones interaction potential for two atoms as a function of separation distance. (Adopted from GROMACS Manual)

Non-bonded interaction potentials are computed on the basis of neighbor lists—these are lists of atoms that are within a certain radius of a given atom—and consist of three terms repulsion, dispersion and a Coulomb term. The Coulomb term characterizes charged interactions, while the repulsion and dispersion term are combined into either a Lennard-Jones or a Buckingham potential. While the Buckingham potential has a relatively more flexible and realistic repulsion term than Lennard-Jones, it is also computationally more expensive—in the scope of our study, due to significant simplifications in the simulated system and to limited computational power, the Lennard-Jones was used. FIGS. 2 and 3 show the relation between distance between atoms (separation distance) and the Lennard-Jones and Coulomb interaction potentials.

Figure 4:
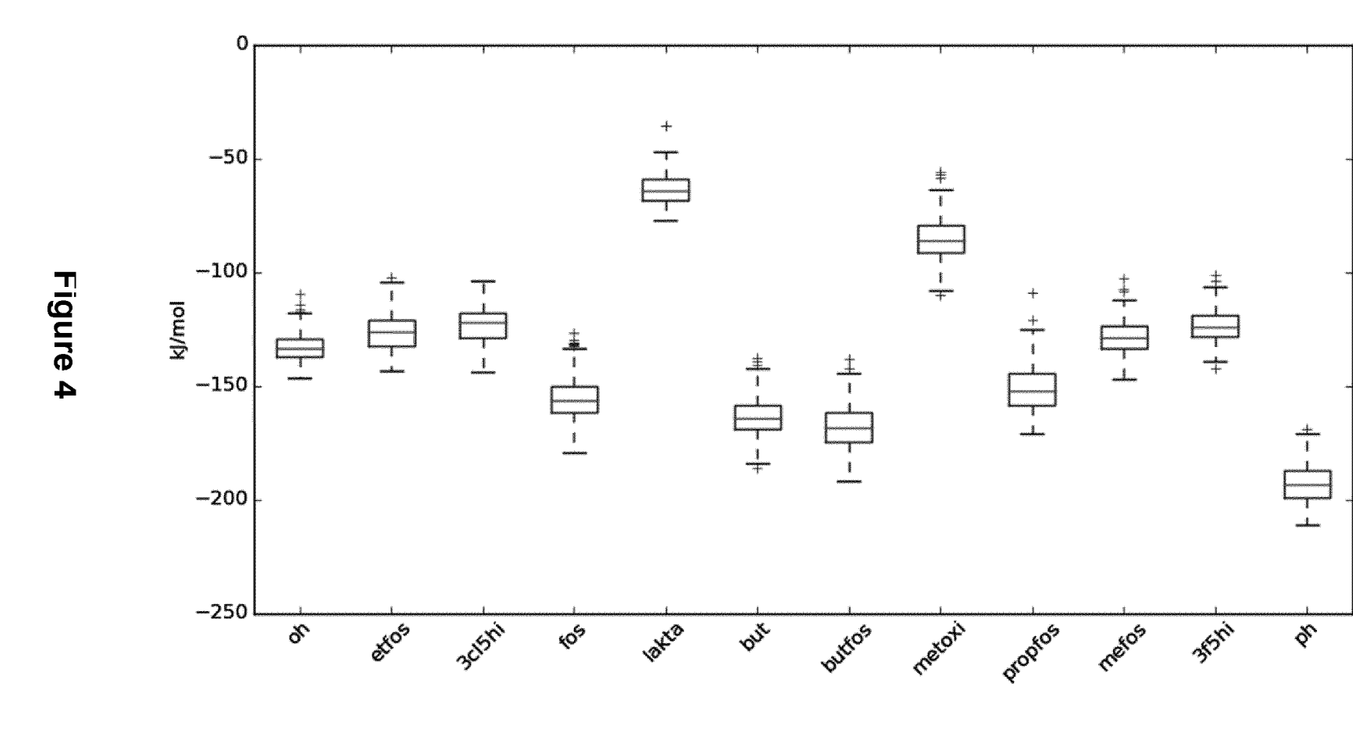
FIG. 4: Lennard-Jones potential energies for the protein-ligand system. The "box and whisker" diagrams illustrate medians—line, upper and lower quartiles—box and the data range—whiskers. Outlying points are represented with "+" signs. Each diagram represents the last 300 data-points after relative convergence.
Figure 5:
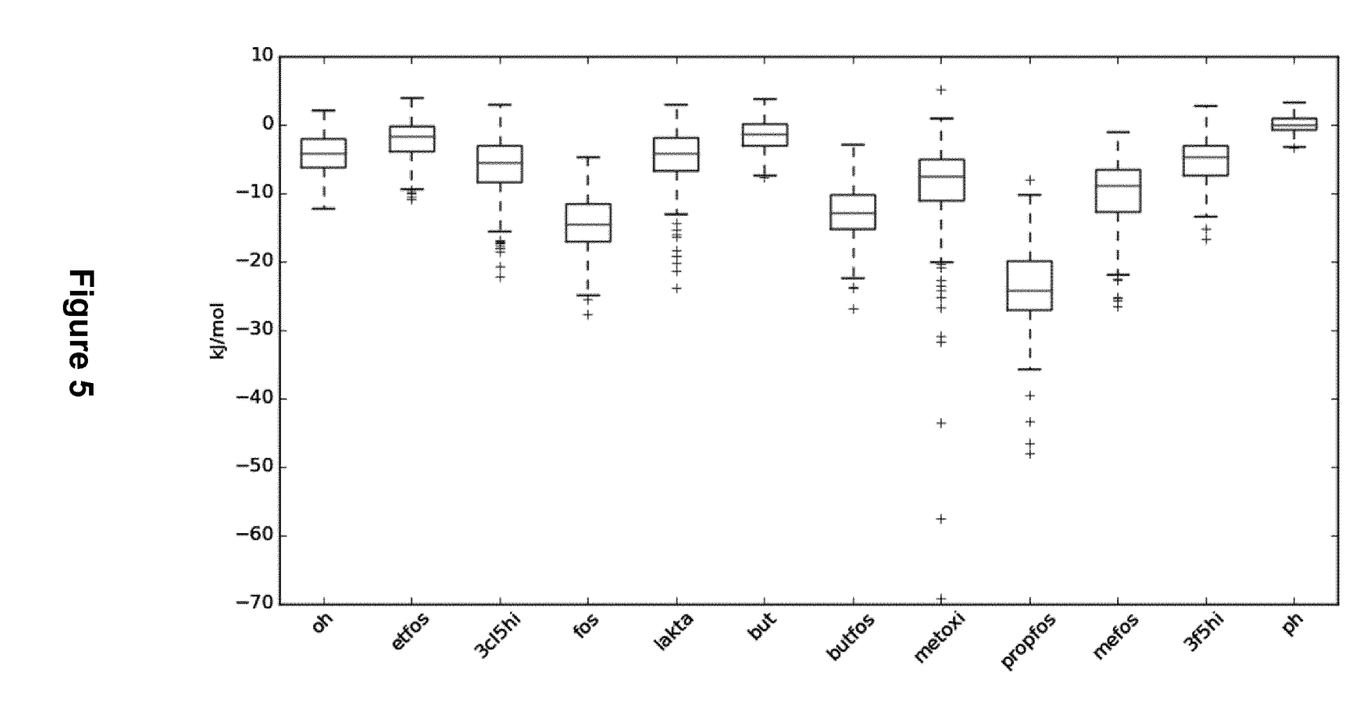
FIG. 5: Coulomb potential energies for the protein-ligand system. The "box and whisker" diagrams illustrate medians—red line, upper and lower quartiles—box and the data range—whiskers. Outlying points are represented with "+" signs. Each diagram represents the last 300 data-points after relative convergence.
Figure 6:
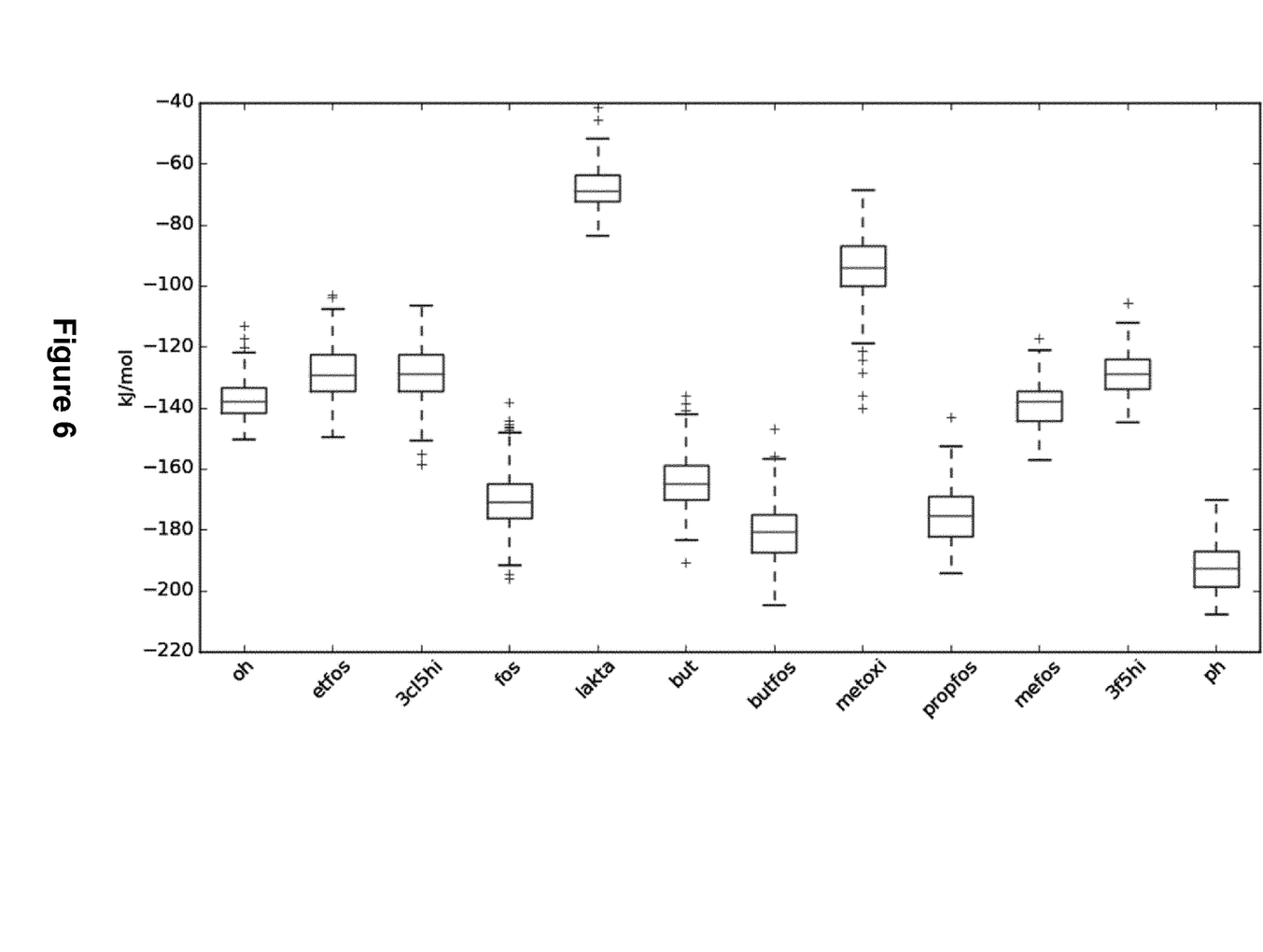
FIG. 6: (Summary image) Summed Lennard-Jones and Coulomb potential energies for the protein-ligand system. The "box and whisker" diagrams illustrate medians—red line, upper and lower quartiles—box and the data range—whiskers. Outlying points are represented with "+" signs. Each diagram represents the last 300 data-points after relative convergence.

After potential energies in all simulated systems converged, short-range Lennard-Jones (LJ) (FIG. 4) and Coulomb (Coul) (FIG. 5) potential energies were extracted for the protein ligand system. In short Coulomb potentials describe interaction between charged particles, while Lennard-Jones between uncharged particles. To give an estimate of the stability of the protein-ligand complex both aspects should be considered—FIG. 6 gives the summations of both LJ and Coul interactions. FIGS. 4, 5 and 6 provide values of the potentials for individual ligands with box and whisker plots illustrating the median, with a box representing the upper and lower quartiles and whiskers representing the data-range. Outlying points are illustrated outside of the whiskers. For this case the cut-off separation distance between non-bonding atoms for Lennard-Jones and Coulomb interactions was arbitrarily set to 0.9 nm, which is the length of approximately 3 water molecules in a linear chain.

The results of MD revealed significant binding energies indicative for ligand binding to GPR81, although previous studies (Dvorak et al., 2012) indicated ligands may not be effective in vivo at al. Therefore, we used an in vivo (in situ) assay based on measuring cytosolic second messenger cAMP in living cells. As described in the previous European Patent Application No. 13 173 446, the cAMP level may, for instance, be determined by fluorescence nano-sensors in the astrocyte. In particular, the cAMP level may be determined by expressing the plasmid for FRET construct Epac1-camps or AKAR2. FRET construct are examined with immersion objective for fluorescent light and confocal microscope or other fluorescent microscope. Cells were excited at 458 nm or other suitable excitation wavelength of light and images are acquired every time interval. Emission spectra are collected from spectral detector or other suitable wavelength of light. Two-channel (CFP and YFP) images are generated from light detector. YFP and CFP fluorescence intensities are quantified within a region of interest selected for individual cell expressing Epac1-camps or AKAR2 using software. FRET signal is reported as the ratio of YFP to CFP fluorescence signal after subtracting the background fluorescence from both YFP and CFP signals. The change in FRET signals reflects change in $[cAMP]_i$.

Results of the MD simulation together with cAMP measurements provide a robust and strong new method for identifying a compound that can be used in mitigating and/or the treatment of a disease associated with abnormal astrocytic function, such as a neuroinflammatory condition.

According to some embodiments, the disease associated with abnormal astrocytic function is a disease selected from the group consisting of: Alzheimer's disease, encephalitis, brain tumours, glioma, brain trauma, concussion, epilepsy, autism, multiple sclerosis, meningoencephalitis, sleep disorders, stroke, Parkinson's disease, spinal cord injury, lipid storage disease.

According to particular embodiments, the disease is Alzheimer's disease.

According to other particular embodiments, the disease is encephalitis.

According to other particular embodiments, the disease is a brain tumour.

According to other particular embodiments, the disease is glioma.

According to other particular embodiments, the disease is brain trauma.

According to other particular embodiments, the disease is concussion.

According to other particular embodiments, the disease is epilepsy.

According to other particular embodiments, the disease is autism.

According to other particular embodiments, the disease is multiple sclerosis.

According to other particular embodiments, the disease is meningoencephalitis.

According to other particular embodiments, the disease is a sleep disorder.

According to other particular embodiments, the disease is stroke.

According to other particular embodiments, the disease is Parkinson's disease.

According to other particular embodiments, the disease is spinal cord injury.

According to other particular embodiments, the disease is lipid storage disease.

Beta-adrenergic receptors, linked to cAMP signaling, strongly inhibit neuroinflammation and lead to multiple sclerosis involving neurodegeneration of oligodendrocytes and other neural cells. Moreover, the main source of noradrenaline, which elicits an elevation in cAMP via beta-adrenergic receptors in astrocytes, arises from locus coeruleus. At an early stage of Alzheimers's disease, a common neurodegenerative disease, the neurons in this nucleus are reduced in numbers, which elicits an elevated neuroinflammatory response. Given that the current standard of care in stroke and neurotrauma patients employ anti-inflammatory drugs (mainly non-steroid anti-inflammatory drugs), treatment of neuroinflammation in neurotrauma via modulating cAMP levels (via GPR81) is considered a new important strategy for neurotherapy. Thus using compounds, described in this invention, are suitable for treatment strategy in the afore-mentioned neuroinflammatory, neurodegenerative and neurotraumatic conditions.

In a further aspect the present invention pertains to an agent elevating the cAMP level in astrocytes for use in mitigating and/or in the treatment of a disease associated with abnormal astrocytic function, such as neurodevelopmental, neurodegenerative, neuroinflammatory and neurotraumatic conditions.

According to some embodiments, a disease associated with abnormal astrocytic function is a disease selected from the group consisting of: Alzheimer's disease, encephalitis, brain tumours, glioma, brain trauma, concussion, epilepsy, autism, multiple sclerosis, meningoencephalitis, sleep disorders, stroke, Parkinson's disease, spinal cord injury, lipid storage disease.

According to particular embodiments, the disease is Alzheimer's disease.

According to other particular embodiments, the disease is encephalitis.

According to other particular embodiments, the disease is a brain tumour.

According to other particular embodiments, the disease is glioma.

According to other particular embodiments, the disease is brain trauma.

According to other particular embodiments, the disease is concussion.

According to other particular embodiments, the disease is epilepsy.

According to other particular embodiments, the disease is autism.

According to other particular embodiments, the disease is multiple sclerosis.

According to other particular embodiments, the disease is meningoencephalitis.

According to other particular embodiments, the disease is a sleep disorder.

According to other particular embodiments, the disease is stroke.

According to other particular embodiments, the disease is Parkinson's disease.

According to other particular embodiments, the disease is spinal cord injury.

According to other particular embodiments, the disease is lipid storage disease.

According to some embodiments, the agent elevating the cAMP level in astrocytes is an agonist for a lactate receptor, such as for the lactate receptor GPR81.

According to certain embodiments, the agent is selected from the group consisting of lactate, such as D-lactate or L-lactate, hydroxybenzoic acid, such as 3-hydroxy benzoic acid, 3-hydroxy-5-substituted benzoic acid, such as 3-Chloro-5-hydroxybenzoic acid (3-Cl-5-HBA), 3-hydroxy butyrate, 3-hydroxy-yoctanoate, and 3H-imidazo[4,5-b]pyridin-5-ols, 4-Methyl-N-(5-(2-(4-methylpiperazin-1-yl)-2-oxoethyl)-4-(2-thienyl)-1,3-thiazol-2-yl)cyclohexanecarboxamide, 4-Methyl-cyclohexanecarboxylic acid {5-[2-(4-methyl-piperazin-1-yl)-2-oxo-ethyl]-4-thiophen-2-yl-thiazol-2-yl}-amide, 4-Methyl-N-(5-(2-(4-methylpiperazin-1-yl)-2-oxoethyl)-4-(5-chloro-thiophen-2-yl)-1,3-thiazol-2-yl)cyclohexanecarboxamide, and 4-Methyl-cyclohexanecarboxylic acid {4-(5-chloro-thiophen-2-yl)-5-[2-(4-methyl-piperazin-1-yl)-2-oxo-ethyl]-thiazol-2-yl}-amide.

According to particular embodiments, the agent is lactate, such as D-lactate or L-lactate.

According to other particular embodiments, the agent is hydroxybenzoic acid, such as 3-hydroxy benzoic acid or 3-hydroxy-5-substituted benzoic acid, such as 3-Chloro-5-hydroxybenzoic acid (3-Cl-5-HBA). According to more specific embodiments, the agent is 3-hydroxy benzoic acid. According to other specific embodiments, the agent is 3-hydroxy-5-substituted benzoic acid, such as 3-Chloro-5-hydroxybenzoic acid (3-Cl-5-HBA).

According to other particular embodiments, the agent is 3-hydroxy butyrate.

According to other particular embodiments, the agent is 3-hydroxy-yoctanoate.

According to other particular embodiments, the agent is a 3H-imidazo[4,5-b] pyridin-5-ol.

According to other particular embodiments, the agent is selected from the group consisting of: 4-Methyl-N-(5-(2-(4-methylpiperazin-1-yl)-2-oxoethyl)-4-(2-thienyl)-1,3-thiazol-2-yl)cyclohexanecarboxamide, 4-Methyl-cyclohexanecarboxylic acid {5-[2-(4-methyl-piperazin-1-yl)-2-oxo-ethyl]-4-thiophen-2-yl-thiazol-2-yl}-amide, 4-Methyl-N-(5-(2-(4-methylpiperazin-1-yl)-2-oxoethyl)-4-(5-chloro-thiophen-2-yl)-1,3-thiazol-2-yl)cyclohexanecarboxamide, and 4-Methyl-cyclohexanecarboxylic acid {4-(5-chloro-thiophen-2-yl)-5-[2-(4-methyl-piperazin-1-yl)-2-oxo-ethyl]-thiazol-2-yl}-amide.

In this connection, also provided is a method for mitigating and/or treating a disease associated with abnormal astrocytic function in a subject (such as human) in need thereof, the method comprises administering a therapeutic effective amount of an agent elevating the cAMP level in astrocytes to said subject.

EXAMPLES

Example 1

MD Approach Validation

Figure 7:
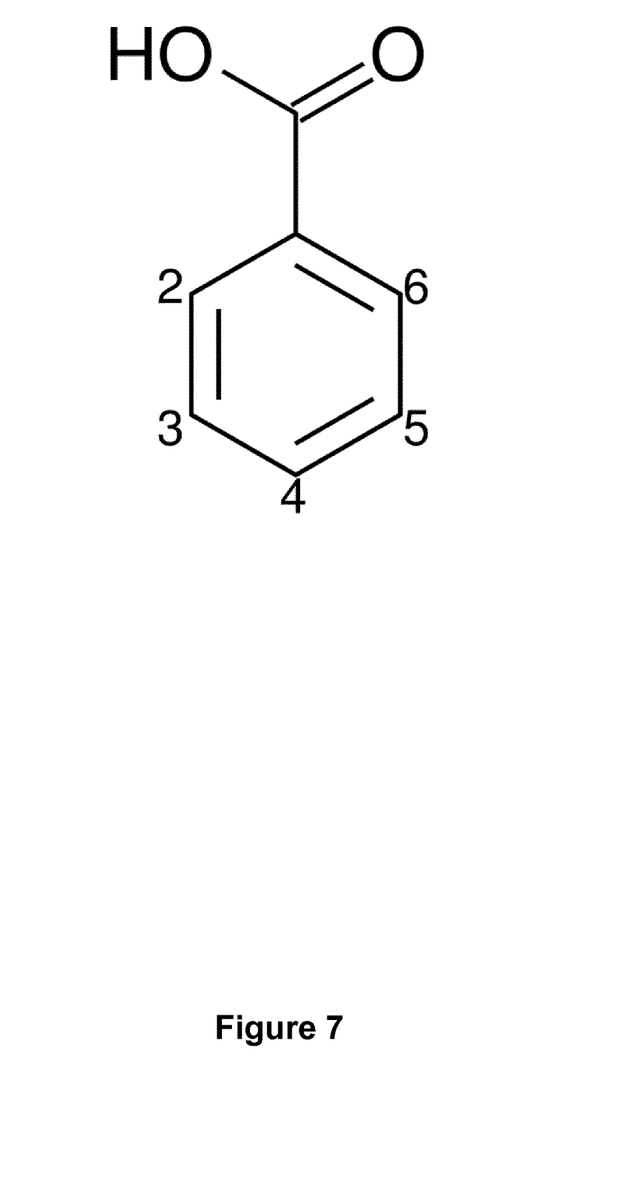
FIG. 7: Numbering schematic for substituents of benzoic acids.
Figure 8:
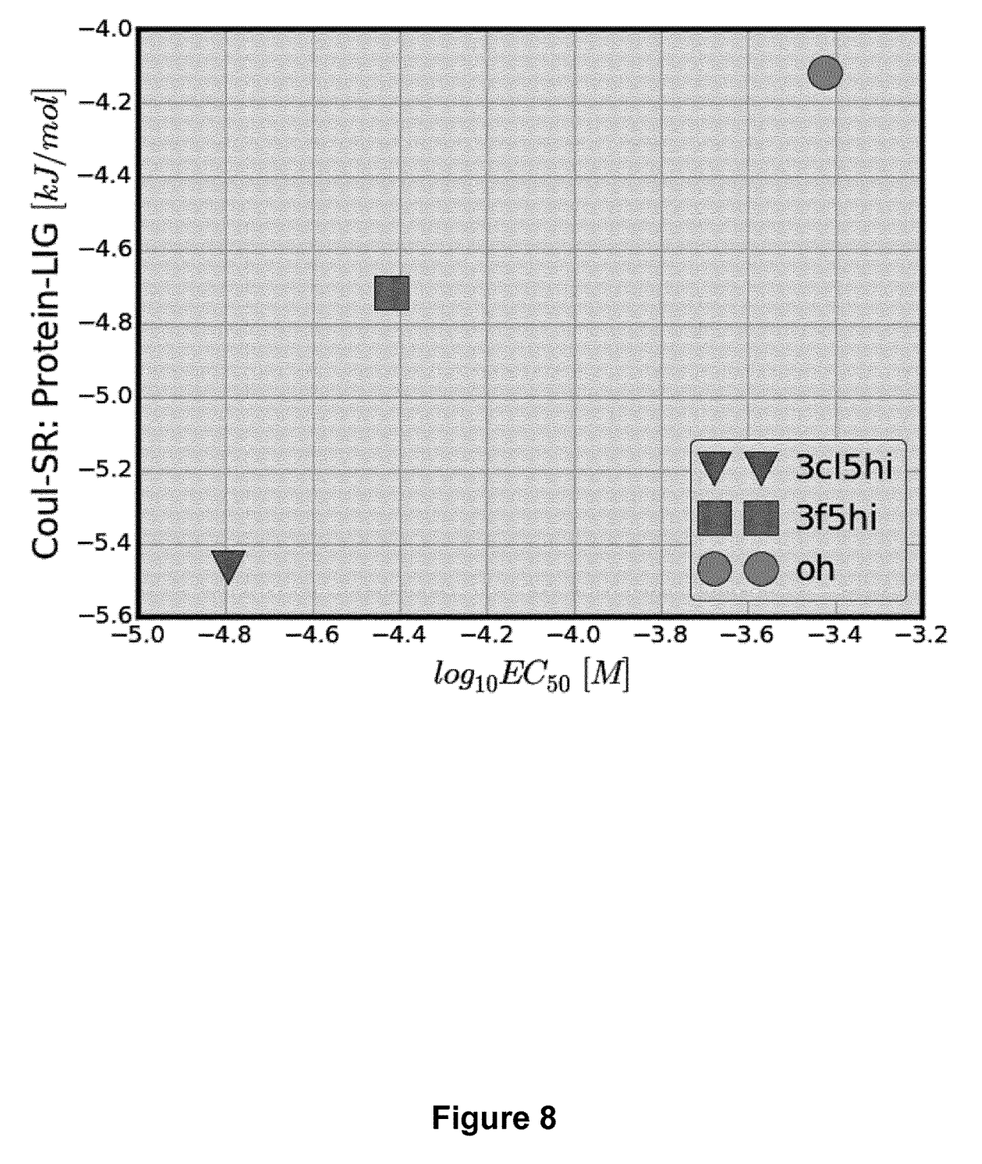
FIG. 8: Relationship between short-range Coulomb interaction potential energies for the protein—ligand system and the $\log_{10}(EC_{50})$ values obtained from Dvorak et al. (2012).

To validate the MD approach we have selected chemically most similar structures from the Table 1, based on benzoic acid derivates differing only in the substituent in position 3 (see FIG. 7). For these molecules, labeled in the present study as: "3c15hi", "3f5hi" and "oh" (Table 1), in a previous study Dvorak et al (2012) determined concentrations at which 50% of its maximal effect is observed for receptor activation in the in vitro assay used, providing an insight into the affinities of several of the molecules. If the affinity of a molecule for a receptor is high, it is fair to assume that the interaction energy is strong—therefore, a deeper potential well should be observed for the receptor-ligand complex (higher stability of the complex). To validate the MD approach we correlated potential energies for the following molecules: "3c15hi", "3f5hi" and "oh" (as referenced in Table 1) to their respective $EC_{50}$ values provided by Dvorak et al (2012). FIG. 8 shows the correlation between short-range Coulomb potential values and $EC_{50}$ values from Dvorak et al, depicting a reasonable correlation of the two parameters and thus validating the MD approach.

Example 2 cAMP Measurements

Figure 9:
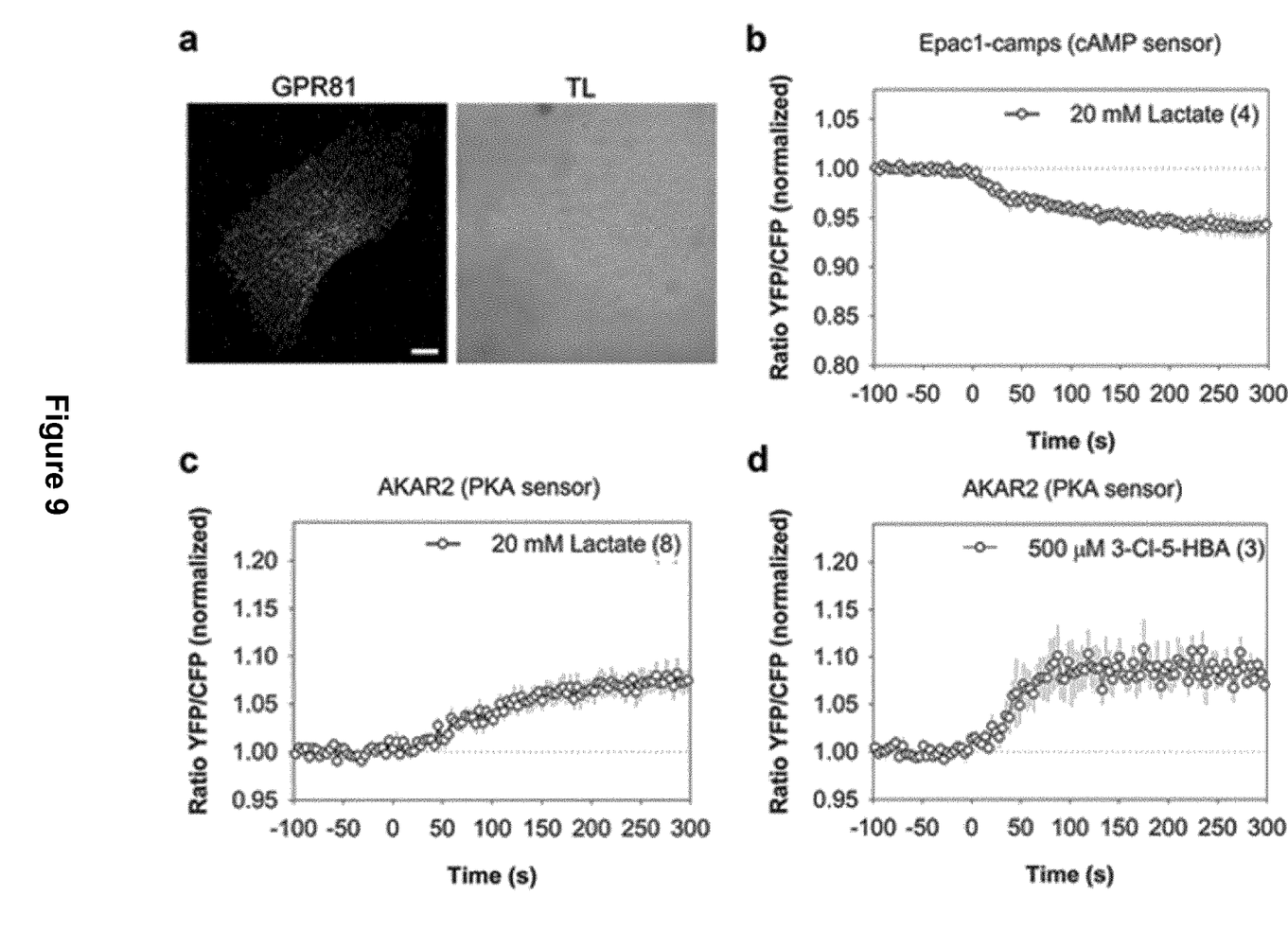

Given that some of the molecules, such as "but" and "metoxi" were determined to be practically ineffective in the assay by Dvorak et al (2012, see Table 2), exhibiting $EC_{50}$ values of >1000 nM, we used them to test whether they would change cAMP (FIG. 9; from European Patent Application No. 13 173 446, FIG. 6). Therefore we determined the responsiveness of cells. These cells responded much better to application of "but" and "metoxi" than to the high affinity molecule "3c15hi" (with $EC_{50}$ value of only 16 µM, see Dvorak et al., 2012).

TABLE 2

Comparison of effectiveness of apparently inefficient GPR81 ligand (according to Dvorak et al., 2012) on cytosolic levels in cAMP in astrocytes.

| Receptor | Stimulus (EC50 Dvorak) | n (%) increase | n (%) decrease | n (%) unresponsive | n all |
|---|---|---|---|---|---|
| GPR81 | "metoxi" (>1000 µM) | 34 (65%) | 3 (6%) | 15 (29%) | 52 |
| | "but" (>1000 µM) | 29 (75%) | 4 (10%) | 6 (15%) | 39 |
| | "3c15hi" (16 µM) | 21 (60%) | 0 (0%) | 14 (40%) | 35 |
| Adrener. | Norepinephrine | 11 (79%) | 0 (0%) | 3 (21%) | 14 |

Here we aimed to provide a set of predictions for the outcomes of in vitro competition tests with a subset of experimentally accessible ligands. The subset consists of two control ligands: 3-chloro-5-hydroxybenzoic acid ("3c15hi") and lactate ("lakta"); for both we know that they bind and elicit a response, and three test ligands: 3-methoxybenzoic acid ("metoxi"), 3-tertbutyl-5-hydroxybenzoic acid ("but") and 3-phenyl-5-hydroxybenzoic acid "ph", for which a relatively high EC50 values were determined (Dvorak et al. 2012) in comparison to those of the ligands from our control subset. These predictions are used next to establish the experiments.

Even though Dvorak et al. (Dvorak et al. 2012), showed only some molecules to be active at concentrations below 1000 µM, this analysis predicts that all the molecules exhibit stability in binding. Therefore one can predict that all of these molecules should produce a cellular response above a certain concentration. The highest stability is obtained by "but", followed by "3c15hi", "metoxi", than "lakta". This result predicts that in competition "but", "3c15hi", "metoxi" should limit the cellular response to "lakta". Therefore, experiments should be performed to test this prediction.

FIG. 7 shows the numbering of substituents in benzoic acids used in this work. According to FIG. 6, we rank the stability of the investigated receptor-ligand complexes. Ligands "lakta", "3c15hi" and "3f5hi"-lactate/lactic acid, 3-chloro-5-hydroxybenzoic acid and 3-fluoro-5-hydroxybenzoic acid were used as positive controls: lactate is an endogenous agonist of GPR81, whereas the other two were found to act as agonists (Dvorak et al. 2012).

Lactate shows the lowest stability in a complex (highest potential energy), ligands "3c15hi" and "3f5hi" show better stability of the protein-ligand complex. Ligands "ph", "but", "fos", "butfos" and "propfos" show the lowest interaction energies and indicate that the complexes they form are relatively more stable than the ones with L-lactate. These ligands can be further subdivided into two separate groups: (phenyl)phosphonic acids and benzoic acids—in both cases the system yielded a lower interaction energy with a longer aliphatic chain present in the system or in the case of "ph" phenyl ring. Crucial points to complex stability are apparently the presence of an electron-acceptor group and a lipophylic substituent, where a longer side-chain on the phosphinic acids indicates a higher complex stability than a shorter one. Interestingly phosphinic acid ligands with the length of the aliphatic side-chain lower than 3 C atoms, indicate lower stability of protein-ligand complexes, while an unsubstituted phosphonic acid again promises a higher stability. In the case of benzoic acids—tertbutyl and phenyl substituents in position 3 show most promise in terms of complex stability.

The results presented previously (Dvorak et al. 2012) showed that "3c15hi" and "3f5hi" are potential agonists for GPR81, as they expressed a relatively low EC50, while "but" and "ph" expressed a high EC50. This may indicate that the position 3-substituent should be limited by size, if a receptor activation is to be observed, growing the size of this substituent, could eventually give rise to two possible scenarios—ligand will bind, there will be no effect, ligand will not bind at all. Our present study points out that the first scenario is a more likely possibility.

Example 3

Cultured astrocytes, e.g. isolated as previously described by Schwartz & Wilson (Glia. 1992; 5(1):75-80) or any other cell type isolated from animal tissues or clonal cell lines derived from human or animal sources are seeded onto coverslips and maintained in an adequate cell cultured medium. All chemicals were from Sigma Aldrich (St. Louis, Mo., USA) unless otherwise noted.

Astrocytes expressing Epac1-camps or AKAR2 FRET construct were examined with a Plan NeoFluoar 40×/1.3 Oil DIC immersion objective (Carl Zeiss, Jena, Germany) and 2-fold zoom factor using Zeiss LSM510 META confocal microscope (Carl Zeiss, Jena, Germany). Cells were excited at 458 nm and images (512×512) were acquired every 3.5 s or 7 s using Lambda stack acquisition. Emission spectra were collected from META detector in eight channels (lambda stack) ranging from 470 nm to 545 nm, each with a 10.7-nm width. Two-channel (CFP and YFP) images were generated from lambda stacks by analytical software "Extract channels". Channels with emission spectra 470- and 481-nm and emission spectra 513-, 524-, and 534-nm were extracted to CFP channel and YFP channel, respectively. YFP and CFP fluorescence intensities were quantified within a region of interest selected for individual cell expressing Epac1-camps or AKAR2 using LSM 510 META software. In the graphs, FRET signal is reported as the ratio of YFP to CFP fluorescence signal after subtracting the background fluorescence from both YFP and CFP signals using Sigma Plot.

The values of FRET signals were normalized (set to 1.0) at the onset of the experiments and averaged. The decrease in FRET signals in Epac1-camps experiments reflects an increase in [cAMP]i and the increase in FRET signals in AKAR2 experiments reflects increase in [cAMP]i.

Initially, astrocytes were kept in standard extracellular solution (10 mM Hepes/NaOH, pH 7.2, 10 mM D-glucose, 131.8 mM NaCl, 1.8 mM CaCl2, 2 mM MgCl2, and 5 mM KCl) and then treated with various reagents following a 100 s baseline.

Example 4

This example shows labeling of cultured astrocytes with antibodies against GPR81 receptor. Astrocytes growing on the cover slips were fixed by 4% paraformaldehyde in phosphate buffer saline for 15 min at room temperature before being treated with 10% goat serum for 1 h at 37° C. Cultures were then stained with primary rat antibodies raised against GPR81 receptor (1:100 dilution, Sigma-Aldrich, St. Louis, Mo., USA) for 2 h at 37° C. After being washed to remove excess primary antibody, the cultures were incubated for 45 min at 37° C. with Alexa Fluor$^{488}$ conjugated secondary antibody (1:600 dilution; Abcam, Cambridge, UK). Excess antibody was removed and cells were treated with SlowFade Gold antifade reagent (Molecular Probes, Invitrogen). Immuno labeled cells were imaged with the inverted Zeiss LSM510 META confocal microscopes with an oil immersion plan apochromatic objective (63×, 1.4 NA; Carl Zeiss, Jena, Germany) using 488-nm Ar-Ion laser excitation. Emission spectra were acquired with a 505-530-nm bandpass emission filter (Alexa Fluor$^{488}$).

REFERENCES

Ahmed K, Tunaru S, Offermanns S. 2009. GPR109A, GPR109B and GPR81, a family of hydroxy-carboxylic acid receptors. Trends Pharmacol Sci 30:557-62.

Ahmed K, Tunaru S, Tang C, Müller M, Gille A, Sassmann A, Hanson J, Offermanns S. 2010. An autocrine lactate loop mediates insulin-dependent inhibition of lipolysis through GPR81. Cell Metab 11:311-9.

Bekker H, Berendsen H J C, Dijkstra J, Achterop S, van Drunen R, van der Spoel D, Sijbers A, Keegstra H, Reitsma B, Renardus M K R. 1992. Gromacs: A parallel computer for molecular dynamics simulations. Physics Computing 92.

Berendsen H J C, van der Spoel R, van Drunen R. 1995. GROMACS: A message-passing parallel molecular dynamics implementation. Comp Phys Comm 91:43-56.

Dvorak C A, Liu C, Shelton J, Kuei C, Sutton S W, Lovenberg T W, Carruthers N I. 2012. Identification of Hydroxybenzoic Acids as Selective Lactate Receptor (GPR81) Agonists with Antilipolytic Effects. ACS Med Chem Lett 3:637-9.

Guex N, Peitsch M C. 1997. SWISS-MODEL and the SWISS-Pdb Viewer: An environment for comparative protein modelling. Electrophoresis 18:2714-2723.

Henke B R, Sparks S M. 2006. Glycogen phosphorylase inhibitors. Mini Rev Med Chem 6:845-57.

Hess B, Kutzner C, van der Spoel D, Lindhal E. 2008. Algorithms for Highly Efficient, Load-Balanced, and Scalable Molecular Simulation. J Chem Theory Comp 4:435-447.

Kiefer F, Arnold K, Künzli M, Bordoli L, Schwede T. 2009. The SWISS-MODEL Repository and associated resources. Nucleic Acids Res 37:D387-92.

Kopp J, Schwede T. 2004. The SWISS-MODEL Repository of annotated three-dimensional protein structure homology models. Nucleic Acids Res 32:D230-4.

Kreft M, Stenovec M, Rupnik M, Grilc S, Krzan M, Potokar M, Pangrsic T, Haydon P G, Zorec R. 2004. Properties of Ca(2+)-dependent exocytosis in cultured astrocytes. Glia 46:437-45.

Kuei C, Yu J, Zhu J, Wu J, Zhang L, Shih A, Mirzadegan T, Lovenberg T, Liu C. 2011. Study of GPR81, the lactate receptor, from distant species identifies residues and motifs critical for GPR81 functions. Mol Pharmacol 80:848-58.

Lauritzen K H, Morland C, Puchades M, Holm-Hansen S, Hagelin E M, Lauritzen F, Attramadal H, Storm-Mathisen J, Gjedde A, Bergersen L H. 2013. Lactate Receptor Sites Link Neurotransmission, Neurovascular Coupling, and Brain Energy Metabolism. Cereb Cortex.

Lindhal E, Hess B, van der Spoel D. 2001. GROMACS 3.0: A package for molecular simulation and trajectory analysis. J Mol Mod 7:306-317.

Liu C, Kuei C, Zhu J, Yu J, Zhang L, Shih A, Mirzadegan T, Shelton J, Sutton S, Connelly M A and others. 2012. 3,5-Dihydroxybenzoic acid, a specific agonist for hydroxycarboxylic acid 1, inhibits lipolysis in adipocytes. J Pharmacol Exp Ther 341:794-801.

Parpura V, Zorec R. 2010. Gliotransmission: Exocytotic release from astrocytes. Brain Res Rev 63:83-92.

Peitsch M C. 1995. Protein Modelling by E-mail. Bio/Techniques 13:658-660.

Pettersen E F, Goddard T D, Huang C C, Couch G S, Greenblatt D M, Meng E C, Ferrin T E. 2004. UCSF Chimera—a visualization system for exploratory research and analysis. J Comput Chem 25:1605-12.

Schwede T, Kopp J, Guex N, Peitsch M C. 2003. SWISS-MODEL: An automated protein homology-modeling server. Nucleic Acids Res 31:3381-5.

Schüttelkopf A W, van Aalten D M. 2004. PRODRG: a tool for high-throughput crystallography of protein-ligand complexes. Acta Crystallogr D Biol Crystallogr 60:1355-63.

van der Spoel D, Lindhal E, Hess B, Groenhof G, Mark A E, Berendsen H J C. 2005. GROMACS: Fast, Flexible and Free. J Comp Chem 26:1701-1718.

Vardjan N, Kreft M, Zorec R. 2014a. Dynamics of (3-adrenergic/cAMP signaling and morphological changes in cultured astrocytes. Glia.

Vardjan N, Kreft M, Zorec R. 2014b. Regulated Exocytosis in Astrocytes Is as Slow as the Metabolic Availability of Gliotransmitters: Focus on Glutamate and ATP. In: Parpura V, Schousboe A, Verkhratsky A, editors. Glutamate and ATP at the interface of metabolism and signaling in the brain: Springer.

Vardjan N, Verkhratsky A, Zorec R. 2015. Pathologic potential of astrocytic vesicle traffic: new targets to treat neurologic diseases? Cell Transplant 24:599-612.

Vardjan N, Zorec R. 2015. Excitable Astrocytes: Ca(2+)- and cAMP-Regulated Exocytosis. Neurochem Res.

Verkhratsky A, Parpura V. 2015. Astrogliopathology in neurological, neurodevelopmental and psychiatric disorders. Neurobiol Dis.

The invention claimed is:

1. A method for identifying a compound useful in mitigating and/or the treatment of a disease associated with abnormal astrocytic function, said method comprising:
   (i) providing a compound;
   (ii) determining that said compound is a ligand for the GPR81 receptor by determining said compound's binding energy with the GPR81 receptor using molecular dynamics simulations and comparing said binding energy to the binding energy determined for a reference compound with the GPR81 receptor; and
   (iii) bringing said compound in contact with a living astrocyte;
   (iv) determining that a steady state change in a cAMP level in said astrocyte contacted with said compound is larger than 3 standard deviations of a signal of cAMP level; and
   (v) identifying the compound as useful in mitigating and/or the treatment of the disease associated with abnormal astrocytic function.

2. The method according to claim 1, wherein said compound is determined to be a ligand for the GPR81 receptor, if it shows a cutoff criterion (CC) of $\geq 1$, estimated by using absolute values of binding energies, using the equation: CC=(binding energy of compound)/(binding energy of reference compound).

3. The method according to claim 1, wherein the disease associated with abnormal astrocytic function is selected from the group consisting of: Alzheimer's disease, encephalitis, brain tumours, glioma, brain trauma, concussion, epilepsy, autism, multiple sclerosis, meningoencephalitis, sleep disorders, stroke, Parkinson's disease, spinal cord injury, lipid storage disease.

4. The method according to claim 1, wherein the reference compound is L-lactate.

* * * * *